United States Patent [19]
Pillai et al.

[11] Patent Number: 5,776,461
[45] Date of Patent: Jul. 7, 1998

[54] COSMETIC COMPOSITIONS CONTAINING PHYTOVITAMIN D

[75] Inventors: Sreekumar Pillai, Wayne, N.J.; Keith Andrew Gottlieb, Houston, Tex.; Anita Marie Brinker, Midland Park; Manisha Mahajan, Westwood, both of N.J.; Anthony Vincent Rawlings, Warrington, England

[73] Assignee: Chesebrough-Pond's USA Co., Division of Conopco, Inc., Greenwich, Conn.

[21] Appl. No.: 690,290

[22] Filed: Jul. 26, 1996

[51] Int. Cl.$^6$ ................................. A61K 35/78
[52] U.S. Cl. .................. 424/195.1; 424/401; 514/844; 514/847
[58] Field of Search ................... 514/844, 847; 424/401

[56] References Cited

U.S. PATENT DOCUMENTS

| | | | |
|---|---|---|---|
| 4,410,515 | 10/1983 | Holick et al. | 424/180 |
| 5,439,935 | 8/1995 | Rawlings et al. | 514/451 |
| 5,476,661 | 12/1995 | Pillai et al. | 424/401 |

FOREIGN PATENT DOCUMENTS

| | | |
|---|---|---|
| 512814 | 11/1992 | European Pat. Off. |
| WO 91/00855 | 1/1991 | WIPO. |
| WO 91/09841 | 7/1991 | WIPO. |

OTHER PUBLICATIONS

MacLaughlin, et al., "Cultured Human Keratinocytes Cannot Metabolize Vitamin $D_3$ to 25-hydroxyvitamin $D_3$" Federation of European Biochemical Societies, vol. 282, No. 2, (May 1991), pp. 409–411.

Tanaka, et al., "1$\alpha$, 25-dihydroxycholecalciferol and a human mycloid leukemia cell line (HL–60)," Biochem J, vol. 204, pp. 713–719, Great Britain (1982).

*Primary Examiner*—Shelley A. Dodson
*Assistant Examiner*—Michael A. Williamson

[57] ABSTRACT

Natural skin care composition containing selected hydroxylated vitamin D compounds or their glycosides, which are derived from plant sources (phytovitamins D). The plant extracts must contain a critical minimum concentration of the phytovitamin D (measured in equivalents of 1,25-(OH)$_2$D in order to induce cell differentiation. In the alternative, phytovitamin D, especially phytovitamin D glycoside, is employed in conjunction with a plant-derived glycosidase.

7 Claims, No Drawings

1

COSMETIC COMPOSITIONS CONTAINING PHYTOVITAMIN D

FIELD OF THE INVENTION

The invention relates to compositions for topical application to human skin containing phytovitamin D, alone or in combination with glycosidases, and methods of using the compositions for treatment and conditioning of the skin.

BACKGROUND OF THE INVENTION

The top layer of human skin or the epidermis is composed of many different cell types including keratinocytes, melanocytes and langerhans cells. Keratinocytes are the major cell type of the epidermis (75–80% of the total number of cells in the human epidermis). Within the epidermis the keratinocytes reside in four distinct stages of differentiation. The basal layer rests on the basal lamina separating epidermis from the dermis. These cells are large columnar rapidly proliferating cells. These basal cells migrate upward within the epidermis, initiated by the process of differentiation. The layer above the basal cells is the spinous layer. The cells in the spinous layer initiate the production of proteins characteristic of the differentiated epidermis. The granular layer, lying above the spinous layer, is characterized by electron-dense granules. This layer is responsible for the synthesis of lipid molecules required for the formation of the water impermeable barrier of the skin. The topmost layer of the skin, the stratum corneum, is formed from the granular layer by the destruction of cellular organelles. The cells in the stratum corneum, corneocytes, contain extensively cross-linked proteins, surrounded by a highly resistant cell envelope. The corneocytes are embedded in a bed of specific lipid structures (analogous to bricks on a bed of mortar) and this structure provides the protective barrier for the skin. The outermost layer of corneocytes is peeled off from the skin during the normal process of desquamation. Differentiation of the epidermal keratinocytes is the driving force for the normal desquamation process to occur. Epidermal differentiation is important for providing the essential function of the skin, namely to provide a protective barrier against the outside environment and to prevent loss of water from the body. Formation of the cornified envelope is the final stage of keratinocyte differentiation. This can be reproduced in keratinocyte cultures in vitro. The rate of formation of cornified envelopes in vitro is thus a good measure of terminal differentiation.

Vitamin $D_3$ is produced in the skin of mammals as the result of solar irradiation which converts 7-dehydrocholesterol into vitamin $D_3$. Vitamin $D_3$ is then metabolized into active biological metabolites. The majority of vitamin $D_3$ is taken up by liver where it is hydroxylated at C-25. The resulting 25-hydroxycholecalciferol (hereinafter "25-D") is then transported to various target organs where further hydroxylation takes place at C-1 or C-24.

Vitamin D, per se, is biologically inactive. Vitamin $D_3$ when applied topically to skin neither has keratinocyte prodifferentiating activity nor is it converted in the skin to 25-D derivative which is a necessary precursor of 1,25-(OH)$_2D_3$ metabolite. See MacLaughlin et al., "Cultured Human Keratinocytes Cannot Metabolize Vitamin $D_3$ to 25-hydroxyvitamin $D_3$," *Federation of European Biochemical Societies*, Vol. 282, No. 2, (May 1991), pp. 409–411. Thus, although numerous cosmetic compositions containing vitamin $D_3$ are known and are available commercially, such compositions do not provide the benefit of 1,25-(OH)$_2D_3$ induced keratinocyte differentiation.

Topical compositions containing 1,25-(OH)$_2D_3$, particularly for psoriasis treatment, are known. See e.g., Morimoto et al., "Topical Administration of 1,25-Dihydroxyvitamin $D_3$ for Psoriasis: Report of Five Cases", *Calcif Tissue Int.*, Vol. 38, (1986), pp. 119–22. See also European Patent Application 512814 which describes cosmetic compositions containing 1-hydroxycholecalciferol and/or 1,25-(OH)$_2D_3$. The composition is said to prevent the damaging effects of ultra-violet light on skin and to promote the repair of photodamaged skin. Pillai et al., U.S. Pat. No. 5,476,661, discloses cosmetic compositions containing 25-(OH)$_2D_3$ and a lipid material.

The term "phytovitamin D" as used herein generally includes hydroxylated forms of vitamin $D_3$ and vitamin $D_2$, such as 25-D and 1,25-(OH)$_2D$ and their glycosides (i.e. one or more of the hydroxy groups of a hydroxylated vitamin D is substituted with a saccharide residue, (e.g. O-glycosyl ester) contained in plant extracts. A more detailed description of the phytovitamin D follows hereinbelow.

PCT patent applications 9109841, 9203414, 9201454, 9115475 and 9100855 (Leo Pharmaceuticals) describe glycosides of vitamin D analogues, but not vitamin D glycosides, and their use for a variety of conditions including skin disorders and skin ageing. U.S. Pat. No. 4,410,515 (Holick et al.) describes the synthesis of vitamin D glycosides and their use in pharmaceutical compositions for the treatment of hypocalcemia and calcium and phosphorus metabolic disorders in humans and animals. The '515 patent discloses various routes of administration, including topical application.

The consumer demand for "natural" based products has been growing in recent years. The consumers perceive chemical synthesis as environmentally unsafe. A chemically synthesized ingredient may contain harsh chemicals. Natural products are perceived as pure and mild and superior to chemically synthesized products. However, delivering a cosmetic benefit from plant sources is not trivial. In order to derive a real benefit from a "natural" source not only a plant containing a specific active has to be identified, but a minimum concentration (which sometimes involves isolating a specific fraction) of that plant has to be identified which truly delivers a cosmetic benefit.

Plant species *Solanum glaucophyllum* and *Cestrum diurnum* which represent two genera of the family Solanaceae (Solanum and Cestrum) have been reported to contain vitamin D glycosides, as well as other forms of vitamin D. See Weissenberg M., "Calcinogenic Glycosides," in Toxicants of plant origin, vol II, pp.202, 215, CRC Press, Inc., Boca Raton, Fla. edited by Cheeke, (1989). Weissenberg described the potential use of these plants for the treatment of vitamin D disorders (no skin disorders mentioned) by a dietary ingestion of the plant. The principle from another plant, *Trisetum flavescens*, has been identified as a 25-glycoside of 1,25-dihydroxyvitamin $D_3$. See Rambeck et al. "A vitamin $D_3$ steroid hormone in the calcinogenic grass *Trisetum flavescens*," Z. Naturforsch., 42c, 430–434 (1987). Leaves from the tomato plant have been reported to contain 1,25D-glycoside activity (Prema et al., "Vitamin D like activity in *Lycopersicon esculentum*," Abstract at the 9th workshop on vitamin D, May 28–Jun. 2, Orlando, Fla., USA, 1993). Mier et al. teach that human skin contains glycosidases which are capable of converting both alpha and beta glycosidic linkages. See Mier et al. "Lysosomal hydrolases of the epidermis: I. Glycosidases," Br. J. Dermatol., 93, 1–10, 1975. Mier et al. do not specifically mention any plant-derived glycosides or vitamin D glycosides.

Almond meal is known to contain several glycosidases including b-glycosidases and extracts of almond meal have been used as a source of glycosidases. See Walsh et al., "Sugars protect desmosome and corneosome glycoproteins from proteolysis." Arch. Dermatol Res., 283: 174 (1991). Rawlings et al. (U.S. Pat. No. 5,439,935) disclose skin care compositions containing a glycosidase (including glycosidases from almonds) and a protease. The glycosidase is said to act on glycoproteins connecting desmosomes; no mention is made of vitamin D or vitamin D glycosidases.

The art discussed above does not teach the use of any vitamin D glycosides from plant sources, alone or in combination with glycosidases, in skin care compositions. The art does not teach topical application of plant extracts containing a phytovitamin D with a specified 1,25-$(OH)_2$-D activity. The art does not teach a cell prodifferentiating activity of the specific plants described herein. The art doesn't teach the use of any plants disclosed herein in cosmetic compositions.

SUMMARY OF THE INVENTION

The present invention includes, in its first aspect, a skin care composition containing:

(i) a plant extract containing a phytovitamin D, wherein the phytovitamin D is present at a concentration of at least 40 ng of 1,25-$(OH)_2$D equivalents per 1 gram of a starting dry plant, said concentration being measured by 1,25-$(OH)_2$D Equivalents Determination Test as described herein; and (ii) a cosmetically acceptable vehicle.

In its second aspect, the present invention includes a skin care composition containing:

(i) from about 0.01% to about 10% of a plant extract containing a phytovitamin D, preferably a vitamin D glycoside;

(ii) from about 0.01% to about 10% of a glycosidase, preferably plantderived; and (iii) a cosmetically acceptable vehicle.

The present invention also includes a method of improving or preventing the appearance of wrinkled, flaky, aged, photodamaged skin and treating skin disorders, which method includes applying to the skin either one of the inventive compositions outlined above.

DETAILED DESCRIPTION OF THE INVENTION:

The present invention provides at least two compositions based on plant extracts containing a phytovitamin D.

The term "phytovitamin D" as used herein includes compounds, which are plant-derived (to satisfy the "natural" character of the present compositions) and which are encompassed by Formula 1:

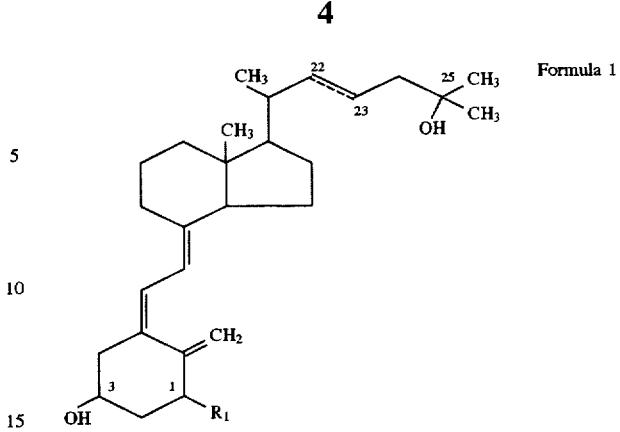

wherein the bond between $C_{22}$ and $C_{23}$ can be a single bond (vitamin $D_3$, cholecalciferol) or a double bond (vitamin $D_2$, ergocalciferol); wherein $R_1$ is selected from H and OH and wherein each hydroxyl group at positions 1, 3, and 25 may be independently substituted with a saccharide residue containing from 1 to 20 saccharide units. The linkage between the steroid and the saccharide residue may be alpha or beta. Cholecalciferol and ergocalciferol are collectively termed herein as "vitamin D". $D_3$ and $D_2$ are both included under the abbreviation "D" herein. The terms "glycosylated Vitamin D" or "glycosylated phytovitamin D" or "vitamin D glycoside" or "phytovitamin D glycoside" as used herein mean that at least one hydroxyl group at positions 1,3 or 25 is substituted with a saccharide residue (i.e., saccharide residue instead of hydrogen in OH groups at the specified positions).

The following plant-derived vitamin D compounds and their glycosylated derivatives are employed according to the present invention: 25-D; 1,25-$(OH)_2$D.

The saccharide residue in formula 1 can contain from 1 to 20 saccharide units per molecule. The linkage between the saccharide units can be alpha or beta. The saccharide units may be glycopyranosyl or glycofuranosyl containing glucose, fructose, galactose or mannose as well as their aminated derivatives. The saccharide units can be linked as straight chains or branched chains, preferably as the straight chains.

A preferred glycosylated phytovitamin D is represented by formula 1 wherein a saccharide residue at position 3 contains from 1 to 10 saccharide units (β-linked to the steroid). The most preferred glycosylated phytovitamin D is represented by Formula 1 wherein a saccharide residue at position 3 contains from 1 to 10 saccharide units (β-linked to the steroid). The preferred saccharide residues are made of 1 to 10 glucose and/or fructose units (αor β-linked to each other).

It has been found, as part of the present invention, that a plant extract has to either contain a phytovitamin D at a specific minimum concentration (first aspect of the invention) or it has to be employed in conjunction with glycosidase (second aspect of the invention), in order to deliver a keratinocyte prodifferentiating activity.

According to the first aspect of the invention, a plant extract is employed in such an amount as to provide a phytovitamin D compound at a concentration of at least 40 ng 1,25-$(OH)_2$D equivalents per 1 gram of a starting dry plant, as measured by 1, 25-$(OH)_2$ Equivalents Determination Test described herein.

The term "dry" as employed herein means dried to a constant weight (e.g., freeze-dried or air-dried).

The HL-60 assay employed herein is specific for 1,25-$(OH)_2$D activity. As part of the Equivalents Determination Test, 25-D will be converted to 1,25-(OH)$_2$D. Pretreatment of the plant extract with glycosidase is also included in the test; such pretreatment ensures that any glycosylated derivatives will be eventually converted to 1,25-(OH)$_2$D and measured in the test.

Put another way, 1,25-(OH)$_2$D is a compound, the measurement of which serves as yardstick, but a plant extract may contain 1,25-(OH)$_2$D or 25-D or glycosylated derivatives thereof. If a plant extract contains 25-D or glycosides of either 25-D or 1,25-(OH)$_2$D, they will be converted in skin to 1,25-(OH)$_2$D. The 1,25-(OH)$_2$D Equivalents Determination Test described in the specification hereinabove ensures that if the plant contains 25-D or vitamin D glycosides, they will be converted to 1,25-(OH)$_2$D and measure, to determine the suitability of such plant extract for use herein.

The phytovitamin D concentration in the plant extract according to the first aspect of the invention is at least 40 ng of 1,25-(OH)$_2$D equivalent per 1 gram of a starting dry plant. The phytovitamin D content is generally in a range of from 40 ng to 50,000 ng of 1,25-(OH)$_2$D equivalent per 1 gram of a starting dry plant, preferably from 40 to 5,000 ng/g, most preferably from 500 to 5,000 ng/g.

1,25-(OH)$_2$D Equivalents Determination Test Used to Determine Suitability of a Plant Extract for Use in the Present Invention:

Differentiation of a promyelocytic leukemia cell line, HL-60 to monocytic/macrophage lineage is promoted by 1,25-(OH)$_2$D. This cell line is very sensitive (nM levels) and specific to 1,25-(OH)$_2$D because other vitamin D analogues such as nonhydroxylated vitamin D or 25D do not induce its differentiation. This test can be utilized to assess the vitamin D content of plant extracts after converting the glycosides and other hydroxylated forms of vitamin D to 1,25-(OH)$_2$D. One can achieve this by following the procedure:

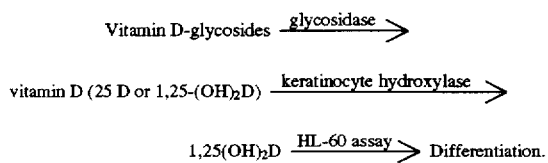

Glycosidases cleave vitamin D glycosides to the aglycone form (free steroid form). After extracting this free vitamin D in chloroform, it is treated with hydroxylase enzyme from keratinocyte homogenate to convert the 25 hydroxy vitamin D (25-D) to the biologically active 1,25-(OH)$_2$D. This can be again extracted into chloroform phase and redissolved in ethanol and tested in the HL-60 cell differentiation assay. Using this procedure, the glycosylated and nonglycosylated forms of 25-D and 1,25-(OH)$_2$D of both vitamin D$_2$ and D$_3$ can be quantitated in HL-60 cell differentiation assay.

a. Plant Extract preparation: The plant extracts are prepared by extracting the dry plant powders with ethanol or other solvents by stirring 1 part of the plant material with 5 to 10 parts of the solvent for 3 to 18 hours at room temperature. Suitable solvents are described hereinbelow. The extracts are clarified by filtration, then dried by evaporation to obtain a dried plant extract.

b. Treatment of Dried Plant Extracts with Glycosidase: 50 mg of dried plant extract are resuspended in 4 ml citrate-phosphate buffer and incubated overnight with a glycosidase enzyme (e.g., from an almond meal extract). After incubation, the mixture is extracted with chloroform. The chloroform phase containing the nonglycosylated vitamin D compounds is dried and resuspended in ethanol at a concentration of 5 mg/ml of ethanol.

c. Hydroxylase Treatment of product of step (b) (Non-Glycosylated Vitamin D Compounds): Human keratinocytes in culture express high amounts of 25(OH) vitamin D 1-a hydroxylase activity. For converting into the 1,25-(OH)$_2$D, which is detected by the product of step (b) in the HL-60 assay, is treated with a keratinocyte homogenate for 1 hour at 37° C. (50 μl of the product of step b with 1 ml of cell homogenate containing 100–200 μg cell protein). After the treatment, the mixture is extracted with chloroform:methanol (1:1), the chloroform phase is dried down, resuspended in ethanol and used in the HL-60 cell differentiation assay.

d. HL-60 Cell Differentiation Assay: The differentiation of HL-60 cells can be assessed by a simple cytochemical method for the expression of non-specific esterase activity (expressed only in the differentiated monocyte/macrophage phenotype) using α-naphthyl acetate as a substrate. HL-60 cell line is obtained (e.g. from American Type Culture Collection (ATCC)) and cultures are established in the laboratory (e.g. using RPMI medium containing 20% fetal calf serum (FCS)). For incubation with the different plant extracts, cells are washed in phosphate buffered saline (PBS), then resuspended in RPMI medium containing 10% FCS and plated at a density of 750,000 cells per 1 ml in 6 well plates. The plates are then treated with either standard 1,25-(OH)$_2$D (0.1 to 100 nM) or the different plant extracts in ethanol, using a maximum ethanol concentration of 5 μl/ml of medium. The cells are treated for 48 hrs before processing for the esterase cytochemical assay.

Expression of nonspecific esterase in HL-60 cells is determined after mounting the cells onto slides using Cytospin. The slides are then fixed in citrateacetone-methanol for 1 min at room temperature, washed in deionized water and air dried for 20 min. The substrate solution for esterase is prepared according to the procedure provided by Sigma by adding 1 capsule of Fast Blue RR salt to 50 ml Trizma buffer (pH 7.6) and 2 ml of α-naphthyl acetate solution. The slides are incubated at 37° C. in this solution for 30 min in the dark. The slides are washed for 3 min in water, counterstained using Mayer's Hematoxylin solution air dried and viewed under microscope. The number of cells showing dark brown precipitate indicating esterase activity is counted and calculated as a percent of the total number of cells in 6 different areas of the slide (approximately 500 total cells). The percent differentiation (% cells showing esterase activity) is compared to the standard 1,25-(OH)$_2$D which typically shows 50% differentiation at 1 nM level. The differentiation induced by the different extracts is compared to the 1,25-(OH)$_2$D standard curve and the 1,25-(OH)$_2$D content of the extract is calculated and expressed as ng 1,25-(OH)$_2$D equivalents/g dry plant.

The plant-derived vitamin D glycosides will be easily accessible to the skin due to their increased solubility. In vivo, the glycosides can be cleaved by the glycosidases present within the skin cells to produce 25-D or 1,25-(OH)$_2$D. The 25-D can then be converted by the skin 1-hydroxylases to the active 1,25-(OH)$_2$D. The 1,25-(OH)$_2$D, provided from the plant sources and that is formed within the skin cells from the plant-derived 25-D or glycosylated form thereof, can then induce differentiation of skin cells.

According to the second aspect of the invention, no minimum concentration of the phytovitamin D is required, but a plant extract is employed in conjunction with a glycosidase. According to the second aspect of the invention, the plant extract preferably contains a glycosylated form of the phytovitamin D, in order to deliver a synergistic keratinocyte pro-differentiating benefit when used in conjunction with a glycosidase.

Plants, the extracts of which are suitable for the inclusion in the inventive compositions (according to both the first and the second aspects thereof), include but are not limited to:

the leaves of the following plants:
*Solanum glaucophyllum*, (a.k.a. *Solanum malacoxylon*)
*Cestrum diurnum*,
*Trisetum flavescens*,
*Fabiana imbricata* (a.k.a. pichi),
*Lycopersicon esculentum* (a.k.a. Tomato)

Solvents suitable for the preparation of plant extract for use herein include, but are not limited to: water, ethanol, methanol, hexane, chloroform, dichloromethane and ethylacetate. The preferred solvents for solubilizing the non-glycosylated vitamin D compounds are ethanol, methanol, chloroform, dichloromethane and hexane. The preferred solvents for solubilizing the vitamin D glycosides are water, ethanol or methanol. The extract may be further concentrated, fractioned, re-extraced or purified, e.g. by organic solvent extraction or by chromatography.

According to the present invention, when the glycosylated forms of phytovitamin D are combined with a glycosidase, a synergistic keratinocyte pro-differentiating effect is attained.

A glycosidase included in the inventive compositions is preferably from a plant source, to keep in line with the "natural" identity of the inventive products. Suitable plant sources include almonds, green coffee beans, spinach, and bakers yeast. Almonds provide a most preferred source because they represent easily available and cosmetically acceptable rich source for both $\alpha$ and $\beta$ glycosidase activity. An extract of the plant in water or ethanol is prepared for the incorporation into inventive compositions.

The inventive compositions typically include from 0.01% to 10%, preferably from 0.05% to 5%, most preferably from 0.1% to 0.5%, by weight of the composition, of a plant extract and from 0.01% to 10%, preferably from 0.05% to 5%, and most preferably from 0.1% to 0.5% of glycosidase.

The inventive compositions also include a cosmetically acceptable vehicle to act as a dilutant, dispersant or carrier for the active ingredients. The vehicle enables the phytovitamins D, alone or in combination with the glycosidase, to be dispersed onto the skin and distributed therein.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from 5 to 99.9%, preferably from 25 to 80% by weight of the emulsion, and can, in the absence of other cosmetic adjuncts, form the balance of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

In a preferred embodiment of the invention, the inventive compositions further include at least one of the following ingredients which are particularly effective in combination with the plant extracts.

Hydroxyacids—enhance proliferation and increases ceramide biosynthesis in keratinocytes, increase epidermal thickness, and increase desquamation of normal skin resulting in smoother, younger looking skin.

The hydroxy acid can be chosen from $\alpha$-hydroxy acids, $\beta$-hydroxyacids, other hydroxycarboxylic acids (e.g., dihydroxycarboxylic acid, hydroxydicarboxylic, hydroxytricarboxylic) and mixtures thereof or combination of their stereoisomers (DL, D or L).

Even more preferably the hydroxy acid is chosen from lactic acid, 2-hydroxyoctanoic acid, hydroxylauric lactic acid, and glycolic acid, and mixtures thereof. When stereo isomers exist, L-isomer is most preferred.

Preferably the amount of the hydroxy acid component present is from 0.01 to 20%, more preferably from 0.05 to 10% and most preferably from 0.1 to 3% by weight.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betains (such as cocoamido propyl betaine).

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, anti-acne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorilloniteclay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,507, incorporated by reference herein.

The following specific examples further illustrate the invention, but the invention is not limited thereto.

EXAMPLE 1

To determine if the different plant species contain 1,25-$(OH)_2D$ like activity, the plant extracts were assayed in 1,25-$(OH)_2D$ receptor binding assay. The receptor binding assay kit was obtained from Amersham. Briefly, the assay measures competition of unknown samples for $^3H$ 1,25-$(OH)_2D$ binding to its specific receptor from chick intestinal cytosol extracts (a rich source for 1,25-$(OH)_2D$ receptors). This assay is very specific for 1,25-$(OH)_2D$ (Other vitamin D analogues react at 100–1000 fold less; 1,25-$(OH)_2D$-glycosides do not show reactivity in this assay). This assay detects as low as 5–10 pg 1,25-$(OH)_2D$ in the extract.

To detect the presence of vitamin D metabolites other than 1,25-$(OH)_2D$ in the plant extracts, vitamin D binding assay was used. This assay detects the presence of 25-D (100%), but also detects to a smaller extent 1,25-$(OH)_2D$ (4%), 24,25$(OH)_2D$ (70%) and nonhydroxyvitamin D (0.4%). This assay utilizes a rat plasma vitamin D binding protein and uses the same principle as the receptor binding assay using competition of unknown samples for $^3H$-25-D binding to the binding protein. The unknown is compared with a standard curve using known amounts of nonlabelled 25-D and the levels of 25-D in the unknown samples are calculated from the standard curve and expressed as ng/g dry plant.

Extracts of the various plant leaves were prepared as follows:

For Solanum and Cestrum, dried powdered leaf material was added to solvent (1 part leaf material to 4–9 parts solvent) and stirred for several hours at room temperature. The solvent was filtered off and replaced with fresh solvent; this was left to stand overnight, then filtered. These steps were repeated one or two times. Cestrum was extracted with ethanol, after a preliminary extraction with chloroform performed in a similar manner. Solanum was extracted with water, then the solid was extracted in a Soxhlet apparatus with ethanol (approx. 8 parts ethanol:1 part solid) for 24 hrs.

Alfalfa, comfrey, peppermint, and olive dried leaf material was extracted in a Soxhlet apparatus for at least 20 hrs with ethanol (1 part leaf material to 10–24 parts solvent). The alfalfa and peppermint material had previously been extracted in a similar manner with hexane, methylene chloride, and ethyl acetate successively; the olive and comfrey with chloroform.

All extracts were dried (ethanol by evaporation under vacuum; water by freeze-drying). The ethanol extracts were used for both the receptor and protein binding assays, except in the case of Solanum, in which the aqueous extract was used.

The amount was calculated from a standard curve using 25-D standard for the protein binding assay and 1,25-(OH)$_2$D standard for the receptor binding assay. The results that were obtained are summarized in Table 1.

TABLE 1

Vitamin D content of the different plant sources determined by receptor binding assays (1,25-(OH)$_2$D) or protein binding assays (mainly D and other vitamin D metabolites)

| PLANT NAME | 25-D/OTHER VITAMIN D (ng/g DRY LEAF) | 1,25-(OH)$_2$D (ng/g DRY LEAF) |
|---|---|---|
| Solanum | 118.4 | 10.0 |
| Cestrum | 55.7 | 14.8 |
| Alfalfa | 46.8 | 21.3 |
| Olive | 74.3 | 12.0 |
| Peppermint | 1.6 | N.D. |
| Comfrey | 1.0 | N.D. |

The data in Table 1 can be used only as a rough estimate of the vitamin D content since the protein and receptor binding assays are not very reliable with crude plant extracts: the presence of other hydrophobic lipids and sterol materials can interfere in the binding giving artificially higher (by competing for the binding of $^3$H-vitamin D) or lower (by blocking the binding of nonlabelled vitamin D) values. But it can be seen from Table 1 that Solanum and Cestrum had a relatively high content of total vitamin D compounds.

EXAMPLE 2

This Example was conducted to ascertain the specificity of HL-60 assay for 1,25-(OH)$_2$D and to construct a standard curve.

Differentiation of a promyelocytic leukemia cell line, HL-60 to monocytic/macrophage lineage is promoted by 1,25-(OH)$_2$D. This cell line is very sensitive and specific to 1,25-(OH)$_2$D and the differentiation can be assayed by a simple cytochemical method for the expression of nonspecific esterase activity using alpha naphthyl acetate substrate using a kit from Sigma Chemical Co. This cell line was obtained from ATCC (American Type Culture Collection).

culture system was established in our laboratory and the assay for differentiation was standardized. Half maximal differentiation was obtained by 1 nM 1,25-(OH)$_2$D and the differentiation ability of 1,25-(OH)$_2$D could be detected as low as 0.1 nM 1,25-(OH)$_2$D in this assay. 25-D; 1,24,25-D (OH)$_3$, non-hydroxylated vitamin D or vitamin D glycosides were inactive at all concentrations pointing to the specificity of 1,25-(OH)$_2$D in this assay.

HL-60 cells were grown in RPMI medium (obtained from Life Technologies, Grand Island, NY) containing 20% FCS (fetal calf serum). The cells were washed, resuspended in medium containing 10% serum at a density of 750,000 cells/ml and treated with the indicated amounts of vitamin D for 48 hrs. Slides were made using Cytospin, cells fixed in the slides by citrate buffered acetone: methanol and air dried for 20 minutes. The slides were stained using Fast Blue RR in Tris buffer containing alpha naphtyl acetate substrate prepared according to the diagnostic kit instructions (Sigma chemical Co). After incubation in the dark for 30 min, slides were rinsed in water, counterstained using hematoxylin, dried and counted in a microscope. 500 cells in a field are counted and the cells containing esterase activity (dark blue precipitate) are scored as a percentage of the total number of cells.

TABLE 2

HL-60 DIFFERENTIATION ASSAY: STANDARD CURVE FOR 1,25-(OH)$_2$D AND SPECIFICITY OF 1,25-(OH)$_2$D

| CONCENTRATION (nM) | % DIFFERENTIATION (1,25-(OH)$_2$D) | % DIFFERENTIATION (25-D) | % DIFFERENTIATION (FREE VITAMIN D$_3$) |
|---|---|---|---|
| 0 | 1 | — | 0 |
| 0.1 | 5 | — | 0 |
| 1 | 50 | 0 | 0 |
| 10 | 90 | 0 | 0 |
| 100 | 95 | 0 | 0 |

It can be seen from the results in Table 2, that 1,25-(OH)$_2$D induces HL-60 cell differentiation in a dose-dependent manner: HL-60 assay is specific for 1,25-(OH)$_2$D and can be used as an easy rapid screening assay for 1,25-(OH)$_2$D-like activity of plant extracts.

EXAMPLE 3

To determine whether the plant extracts showing 1,25-(OH)$_2$D-like activity in the binding assays (Table 1) have differentiation-stimulating activity, extracts were tested in the HL-60 cell differentiation assay described in Example 2. The Cestrum ethanol extract was the same as in Example 1. The chloroform/methanol extract was prepared as follows: fresh Cestrum leaves were freeze-dried and the dried leaves ground in a blender with chloroform. The material was filtered, then ground with chloroform again; this process was repeated until the extracts were nearly colorless. The solid was then extracted repeatedly with methanol/chloroform 2:1, by blending and then by stirring. The combined methanol/chloroform extracts were evaporated to dryness.

Dried Trisetum leaves were stirred with ethanol at room temperature (1 part leaf: 11 parts ethanol) several hours, then filtered. The stirring and filtration steps were repeated twice.

The extracts were dried and partitioned between water and methylene chloride. The methylene chloride fraction was dried and partitioned between hexane and methanol:water, 9:1. The methanol:water fraction (referred to as the methanol extract) was dried and used for the HL-60 assay.

All extracts were dissolved in ethanol for assay. The differentiation results that were obtained are summarized in Table 3.

TABLE 3

1,25-$(OH)_2$D CONTENT OF PLANT EXTRACTS MEASURED BY HL-60 CELL DIFFERENTIATION ASSAY

| PLANT SOURCE | % DIFFERENTIATION | 1,25-$(OH)_2$D CONTENT (ng/g DRY LEAF) |
|---|---|---|
| Cestrum (ethanol) | 5 | 123.4 |
| Cestrum (CHCl$_3$/MeOH) | 10 | 177.6 |
| Trisetum (methanol) | 7 | 18.3 |

Cestrum and Trisetum extracts had 1,25-$(OH)_2$D like differentiation activity. A commercially prepared Pichi extract was also active (data not shown). For Cestrum, chloroform/methanol extract showed higher activity than the ethanol extract suggesting greater solubility of the phytovitamin D from this plant in chloroform/methanol than in ethanol.

EXAMPLE 4

To determine the minimum amount of 1,25-$(OH)_2$D like activity required in a plant extract in order to induce HL-60 differentiation, the crude plant extracts were fractionated using HPLC. A Waters Delta-Prep 3000 system was used with a Waters Delta-Pak $C_{18}$, 25×100 mm column (300 angstrom, 15 μm packing) preceded by a Guard-Pak $C_{18}$ column with the same packing. Samples were eluted with a linear gradient of 100% water to 100% acetonitrile in 60 min, at a flow rate of 12 ml/min and 0.6 min/fraction. Detection was with a Waters 990 photodiode array detector. Dried ethanol extracts (the same as used in Example 1) of Solanum and Cestrum were dissolved in ethanol (100 mg extract/5 ml ethanol) and the sample filtered before injection into the HPLC. Fractions were pooled as indicated in Tables 4A and 4B and evaporated to dryness, then redissolved in ethanol at a concentration of 5 mg/ml and the HL-60 assay carried out.

Vitamin D compounds can be separated from glycosides, the chlorophyll fraction and hydrophobic lipids. The glycosides elute in earlier fractions (15–80) followed by non-glycosylated vitamin D compounds (from 80–130) followed by hydrophobic substances (160–200).

TABLE 4A

HL-60 CELL DIFFERENTIATION ASSAY USING THE DIFFERENT HPLC FRACTIONS FROM CESTRUM ETHANOL EXTRACT

| HPLC FRACTION (of EtOH extract) | % DIFFERENTIATION | ng 1,25-$(OH)_2$D IN FRACTION | 1,25-$(OH)_2$D (ng/g DRY LEAF) |
|---|---|---|---|
| 1–21 | 0 | — | — |
| 22–47 | 5 | 21.2 | 16.3 |
| 48–100 | 12 | 25.2 | 19.4 |
| 101–130 | 10 | 6.2 | 4.8 |
| 131–168 | 1 | 4.0 | 3.1 |
| 169–200 | 0 | 0 | 0 |

The first pooled fractions (from 1–21) containing mainly the vitamin D glycosides showed no differentiation promoting activity. Fractions 2 and 3 (fraction numbers 22–100) containing most of the free vitamin D compounds show prodifferentiating activity. Fraction 4 and beyond (fraction numbers 100 and beyond) which contain mostly the hydrophobic lipids had very little activity. Similar results were also observed for ethanol extract from Solanum (Table 4B).

TABLE 4B

HPLC FRACTIONS FROM *SOLANUM GLAUCOPHYLLUM* ETHANOL EXTRACT

| HPLC FRACTION (of Ethanol extract) | % DIFFERENTIATION | ng 1,25-$(OH)_2$D IN FRACTION | 1,25-$(OH)_2$D (ng/g DRY LEAF) |
|---|---|---|---|
| 1–19 | 5 | 8.3 | 8.05 |
| 20–64 | 15 | 10.7 | 10.38 |
| 65–93 | 7 | 64.2 | 62.3 |
| 94–120 | 2 | 8.3 | 8.05 |
| 121–156 | 0 | 0 | 0 |
| 157–200 | 0 | 0 | 0 |

The minimum of differentiation in fractions 1–19 (corresponding to where the glycosides are eluted) suggests that HL-60 cells respond only minimally to 1,25-$(OH)_2$D- glycoside and these cells do not generate the glycosidase required to convert the 1,25-(OH)$_2$D-glycosides to 1,25-(OH)$_2$D. Assuming that essentially all the vitamin D elutes in fractions 20–120, the total amount of vitamin D material per g dry weight of the leaf corresponds to approximately 40 ng 1,25-(OH)$_2$D equivalent/gram dry wt. for Cestrum and approximately 80 ng for Solanum. This experiment also indicates that a plant extract containing 40 ng or higher equivalent of nonglycosylated 1,25-(OH)$_2$D per gram of dry plant is required for the prodifferentiating activity.

From the above data it can be concluded that a plant extract containing 40 ng or above of 1,25-(OH)$_2$D/gram of dry plant is capable of inducing cell differentiation.

EXAMPLE 5

To assess the total 1,25-(OH)$_2$D (glycosylated and nonglycosylated) in the plant extract, the different plant extracts were hydrolyzed using almond meal extract (containing glycosidase) and the differentiation ability was assessed.

Almond meal (obtained from Lipo Chemicals) was homogenized (0.6 g in 5 ml) in citrate-phosphate buffer (pH 5.0), centrifuged for 5 min at 2500 rpm and filtered through a 0.2 μm filter. The supernatant was incubated with the different plant extracts for 18 hrs as described in the 1,25-(OH)$_2$D Equivalents Determination Test (section on glycosidase treatment). The incubation mixtures included 50 mg plant extract dissolved in 4 ml buffer plus 1 ml almond enzyme preparation. As controls, samples were prepared and incubated in the same way but with 1 ml buffer in place of the almond enzyme preparation. For Solanum and Trisetum, a commercial preparation from snail (beta-glucuronidase type H-3 from Helix pomatia, Sigma) was used instead of the almond prep; 50 μl was added to 5 ml buffer in which 50 mg plant extract had been dissolved. After the incubation, the mixture was extracted with chloroform, the chloroform phase was dried, resuspended in ethanol and the ethanolic extract was tested in the HL-60 cell differentiation assay.

Activity in samples without added enzyme would be due to any non-glycosylated 1,25-(OH)$_2$D present; activity in samples with enzyme would be due to non-glycosylated 1,25-(OH)$_2$D already present plus any generated by hydrolysis of 1,25-(OH)$_2$D glycosides. Thus the difference in vitamin D levels between hydrolyzed and control samples indicates the level of 1,25-(OH)$_2$D glycosides present. Percent differentiation of plant extracts was measured before treatment with almond meal extract (only 1,25-(OH)$_2$D detected) and after the treatment with almond meal extract (1,25-(OH)$_2$ and its glycosylated forms detected).

The results that were obtained are summarized in Table 5.

TABLE 5

| PLANT SOURCE | % DIFFERENTIATION | ng 1,25-(OH)$_2$D/g DRY LEAF |
|---|---|---|
| Cestrum (CHCl$_3$/MeOH) | | |
| 1,25-(OH)$_2$D | 5 | 30 |
| 1,25-(OH)$_2$D + its glycosides | 40 | 176 |
| Solanum (H$_2$O) | | |
| 1,25-(OH)$_2$D | 10 | 32.1 |
| 1,25-(OH)$_2$D + its glycosides | 75 | 749 |
| Pichi** | | |
| 1,25-(OH)$_2$D | 12 | 18 ng/g extract |
| 1,25-(OH)$_2$D + its glycosides | 27 | 62.4 (ng/g extract) |
| Trisetum (MeOH) | | |
| 1,25-(OH)$_2$D | 7 | 15.9 |
| 1,25-(OH)$_2$D + its glycosides | 25 | 41.9 |
| Almond meal extract only | 0 | 0 |

**Pichi is a commercially available ethanol extract.

As seen in Table 5, the differentiation ability was greatly enhanced after the digestion with almond meal or snail enzyme prep. The almond meal control by itself had no differentiation inducing activity, suggesting that the glycosidase of the almond meal hydrolyses the 1,25-(OH)$_2$D-glycosides of the plant releasing free 1,25-(OH)$_2$D which is responsible for the increased differentiation activity of the almond meal incubated samples. In this assay, the amount of non-glycosylated 1,25-(OH)$_2$D varied between 16 to 32 ng/g dry leaf and the total 1,25-(OH)$_2$D (after almond meal treatment) varied between 40 and 750 ng/g dry leaf.

EXAMPLE 6

To determine whether the plant extracts containing vitamin D can induce keratinocyte differentiation, the effects of the various plant extracts before and after almond extract treatment (as explained in Example 5) were tested for the formation of cornified envelopes, a marker for terminal differentiation of keratinocytes. In this method, keratinocytes were treated with the various extracts dissolved in ethanol (as described for the HL-60 assay) for 48 hrs in the presence of 5 uCi of 35S methionine included in the medium. The labelled methionine gets incorporated into the newly synthesized proteins during this 48 hr. period, including the proteins required for the formation of cornified envelopes. At the end of the 48 hrs., the cells were washed and incubated for 3 hrs with 1.8 nM CaCl$_2$ and 5 uM ionomycin, a calcium ionophore. This treatment allows Ca to flow into the cells, maximally activate the enzyme transglutaminase and crosslinks all the labelled cornified envelope precursor proteins to form labelled cornified envelopes. The cells were then dissolved in 2%SDS/40 mM DTT, and the amount of insoluble cornified envelopes was quantitated by scintillation counting after separating from the soluble proteins by filtration on 0.2 micron filters.

The results that were obtained are summarized in Table 6.

TABLE 6

Cornified enveloper formation of adult human keratinocytes using hydrolyzed and non hydrolyzed plant extracts

| PLANT EXTRACT | NO HYDROLYSIS (no almond meal extract) (% of control) | WITH HYDROLYSIS (+ almond meal extract) |
|---|---|---|
| Control | 100 ± 3.04 | 105.1 ± 7.9 |
| 1 nM 1,25-OH$_2$D | 207.6 ± 7.9 | — |

TABLE 6-continued

Cornified enveloper formation of adult human keratinocytes using hydrolyzed and non hydrolyzed plant extracts

| PLANT EXTRACT | NO HYDROLYSIS (no almond meal extract) (% of control) | WITH HYDROLYSIS (+ almond meal extract) |
|---|---|---|
| Cestrum ethanol extract | 82.14 ± 20.5 | 132.2 ± 17.5* |
| Cestrum CHCl₃/MeoH extract | 64.62 ± 4.56 | 112.55 ± 4.83* |
| Solanum ethanol extract | 56.54 ± 20.58 | 115.71 ± 16.11* |
| Pichi ethanol extract | 108.12 ± 10.3 | 114.2 ± 0.378 |

*Statistically significant increase in differentiation after hydrolysis (p <0.01).

The results in Table 6 show that glycosidase treatment increased the differentiation ability of the plant extracts in keratinocytes indicating the release of nonglycosylated 1,25-(OH)$_2$D from the plant extracts by the almond meal glycosidases. The extracts without hydrolysis had no differentiation inducing activity (actually inhibited differentiation in some cases) probably due to the presence of other phyto-compounds in the extract. In all cases, glycosidase treatment increased the cornified envelope formation significantly compared to the untreated control. The almond meal extract by itself was inactive.

Example 6 demonstrates the potentiation of differentiation action of the phytovitamin D containing plant extracts upon the addition of glycosidase. In all cases, glycosidase potentiated the activity of the plant extract on keratinocyte cornified envelope formation.

The plants used in the examples above were obtained from the following sources: Dried Solanum and Cestrum material were gifts from Dr. R. Wasserman, Cornell University; fresh Cestrum material was collected for us by Mr. George Gann, Ecohorizons, Miami, Fla. Dried Trisetum was a gift from Dr. W. Rambeck, Munich, Germany. The Pichi extract is commercially available from Active Organics, Dallas, Tex. as Actiphyte™ of Pichi. Dried plant material of alfalfa, olive, peppermint, and comfrey is available from many suppliers of botanicals. The olive and comfrey leaves used in these Examples were obtained from Wilhelm Kr amer, Schwebheim, Germany; the peppermint from Heinrich Ambrosius GmbH, Hamburg, Germany, and the alfalfa from Weinstein Nutritional Products and Botanicals International.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin care composition comprising:
   (i) from about 0.01% to about 10% of a plant extract containing a phytovitamin D;
   (ii) from about 0.01% to about 10% of a glycosidase; and
   (iii) a cosmetically acceptable vehicle;
   wherein the plant is selected from the group consisting of Solanum glaucophyllum, Cestrum diurnum, Trisetum flavescens, Fabiana imbricata, Lycopersicon esculentum.

2. The composition of claim 1 wherein the phytovitamin D is a phytovitamin D glycoside.

3. The composition of claim 1 wherein the glycosidase is derived from a plant.

4. A method of treating a skin disorder selected from the group consisting of wrinkled, flaky, aged, and photodamaged skin, which method includes applying to the skin a composition according to claim 1.

5. A method of treating a skin disorder selected from the group consisting of wrinkled, flaky, aged, and photodamaged skin, which method includes applying to the skin a composition according to claim 1.

6. A skin care composition comprising:
   (i) from about 0.01% to about 10% of a plant extract containing a phytovitamin D glycoside;
   (ii) from about 0.01% to about 10% of a glycosidase; and
   (iii) a cosmetically acceptable vehicle.

7. A method of treating a skin disorder selected from the group consisting of wrinkled, flaky, aged, and photodamaged skin, which method includes applying to the skin a composition according to claim 6.

* * * * *